US006849162B2

(12) United States Patent
Teles et al.

(10) Patent No.: US 6,849,162 B2
(45) Date of Patent: Feb. 1, 2005

(54) METHOD FOR THE PRODUCTION OF PROPYLENE OXIDE

(75) Inventors: Joaquim Henrique Teles, Otterstadt (DE); Alwin Rehfinger, Mutterstadt (DE); Peter Bassler, Viernheim (DE); Anne Wenzel, Eggenstein-Leopoldshafen (DE); Norbert Rieber, Mannheim (DE); Peter Rudolf, Ladenburg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/312,884

(22) PCT Filed: Jul. 5, 2001

(86) PCT No.: PCT/EP01/07717

§ 371 (c)(1),
(2), (4) Date: Jan. 2, 2003

(87) PCT Pub. No.: WO02/02545

PCT Pub. Date: Jan. 10, 2002

(65) Prior Publication Data

US 2003/0146080 A1 Aug. 7, 2003

(30) Foreign Application Priority Data

Jul. 6, 2000 (DE) .......................................... 100 32 885

(51) Int. Cl.[7] .......................... B01D 3/34; C07D 301/32; C07C 27/28
(52) U.S. Cl. ............................ 203/38; 203/78; 203/80; 203/DIG. 21; 203/DIG. 23; 203/14; 549/531; 549/541; 568/913
(58) Field of Search ............................. 203/29, 38, 14, 203/18, 78, 80, DIG. 21, DIG. 23, 66; 568/913; 549/541, 531, 542

(56) References Cited

U.S. PATENT DOCUMENTS

| 3,350,417 | A |   | 10/1967 | Binning et al. |
| 3,715,284 | A |   | 2/1973  | Burns et al. |
| 3,838,020 | A |   | 9/1974  | Kageyama et al. |
| 3,881,996 | A |   | 5/1975  | Schmidt |
| 5,006,206 | A | * | 4/1991  | Shih et al. ................. 203/55 |
| 5,106,458 | A |   | 4/1992  | Meyer et al. |
| 5,107,002 | A |   | 4/1992  | Shih |
| 5,133,839 | A | * | 7/1992  | Shih ........................... 203/64 |
| 5,139,622 | A | * | 8/1992  | Marquis et al. ............. 203/64 |
| 5,354,430 | A | * | 10/1994 | Culbreth et al. ............. 203/64 |
| 5,489,366 | A |   | 2/1996  | Jongenburger |

FOREIGN PATENT DOCUMENTS

| DD | 215 084   | 10/1984 |
| EP | 0 524 816 | 1/1993  |

* cited by examiner

Primary Examiner—Virginia Manoharan
(74) Attorney, Agent, or Firm—Oblon, Spivak, McClelland, Maier & Neustadt, P.C.

(57) ABSTRACT

A process for the preparation of propylene oxide in the presence of methanol, in which propylene oxide is separated from a mixture propylene oxide and methanol, and the resultant methanol containing mixture is worked up, including seperating methanol from a mixture comprising methanol and methyl formate during the work-up.

22 Claims, No Drawings

METHOD FOR THE PRODUCTION OF PROPYLENE OXIDE

The present invention relates to a process for the preparation of propylene oxide in which methanol is employed. In the process according to the invention, methanol is worked up and separated off from a mixture comprising methanol and methyl formate.

In the standard processes of the prior art in which propylene oxide is prepared in the presence of methanol, methyl formate is generally formed in at least one process step from methanol and/or from propylene oxide. The problem occurs in particular if the target product propylene oxide has to be separated from the undesired by-product methyl formate and, owing to the very similar boiling points of these two compounds, high equipment complexity is necessary for the separation. In the distillation methods normally employed in this respect, extractive distillation methods, for example, are accordingly necessary in order to ensure the requisite target-product purities.

Complex methods of this type for the separation of methyl formate from propylene oxide are described, for example, in U.S. Pat. No. 5,107,002 and U.S. Pat. No. 5,106,458.

It is an object of the present invention to provide a process which enables less equipment complexity and ensures more efficient and inexpensive preparation of propylene oxide.

We have found that this object is achieved by a process for the preparation of propylene oxide in the presence of methanol, in which propylene oxide is separated off from a mixture comprising propylene oxide and methanol, and the resultant mixture comprising methanol is worked up, which comprises separating methanol off from a mixture comprising methanol and methyl formate during the work-up.

The separation of the methanol from the mixture comprising methyl formate and methanol can in principle be achieved by any conceivable method, so long as it is ensured that the purity of the methanol separated off meets the requirements made.

Mention may be made here, inter alia, of chemical methods. For example, it is possible to bring the mixture comprising methanol and methyl formate into contact with a suitable basic ion exchanger, which results in the formation of methanol, with the formate remaining on the ion exchanger. This method is described, inter alia, in U.S. Pat. No. 5,107,002.

Furthermore, it is possible to treat the mixture comprising methanol and methyl formate with a base, during which the methyl formate is hydrolyzed. Use can be made here of all bases by means of which the hydrolysis of the methyl formate can be achieved. Preference is given to strong bases. Particularly preferred bases which may be mentioned for the purposes of the present invention are salts of acids which are weaker acids than formic acid. Mention may preferably be made here, for example, of, inter alia, alkali metal and alkaline earth metal hydroxides or alkali metal salts of alcohols or phenols. It is of course also possible to employ mixtures of two or more of these bases.

Preference is furthermore given to the separation of methanol from the mixture comprising methanol and methyl formate using physical methods, for example distillation methods.

Of these, extractive distillation methods, for example, are possible, as are known from the prior art and mentioned, for example, in the above-mentioned U.S. Pat. No. 5,107,002. However, preference is given to distillation methods which can be implemented with less equipment complexity than said extractive distillation methods.

Preference is given to a distillation method in which one or more columns, preferably one column, is employed. If one column is employed, this has at least 5, preferably at least 10 and in particular at least 20 theoretical plates.

The pressures preferably used are generally in the range from 0.2 to 50 bar, preferably in the range from 1.5 to 30 bar and in particular in the range from 2.0 to 20 bar.

The top and bottom temperatures are clearly determined by the selected pressure. In a particularly preferred embodiment, this column, which has approximately 20 theoretical separation stages, is generally operated in the range from 0.2 to 50 bar, preferably in the range from 1.5 to 30 bar and very particularly preferably in the range from 2.0 to 20 bar. The top product obtained is a mixture comprising methyl formate and a small proportion of the methanol present in the feed. In general, the resultant mixture has a methanol content of less than 80% by weight, preferably less than 50% by weight and particularly preferably less than 20% by weight.

The present invention therefore also relates to a process as described above wherein the separation of the methanol from the mixture comprising methanol and methyl formate is carried out in a distillation column having at least five theoretical plates at pressures in the range from 0.2 to 50 bar.

It is furthermore conceivable for the mixture comprising methanol and methyl formate additionally to have further components besides methyl formate. The term "components" here denotes both pure compounds and azeotropes which have a boiling point which is lower than the boiling point of methanol. Components of this type which may be mentioned by way of example are, inter alia, acetaldehyde, 1,1-dimethoxyethane, propionaldehyde, 1,1-dimethoxypropane, acetone and 2,4-dimethyl-1,3-dioxolane. These may likewise be separated off from the mixture in the course of the work-up.

It is thus possible to separate these by-products off from the mixture by one or more suitable physical or chemical methods before separation of the methanol from the methyl formate. It is likewise possible firstly to separate methanol from the mixture, which can result in a mixture comprising methanol and at least one impurity. In this case, the separation of methanol from the mixture may be followed by one or more separation stages in which methanol is separated off from the at least one impurity. The separation of methanol from the mixture can likewise result in a mixture comprising methyl formate and one or more impurities. This too can, if necessary, be separated into its constituents by one or more suitable physical or chemical methods. The constituents can then be fed, separately or together, to one or more further processes as starting materials or subjected to heat recovery.

Depending on the chemical nature of the impurities, it is also possible to separate methanol from the mixture by separating both methyl formate and the at least one impurity from the methanol in a single process step.

The above-described distillation, which is preferentially employed in accordance with the invention, gives a methanol fraction which has a methyl formate content of, in general, less than 500 ppm, preferably less than 100 ppm and particularly preferably less than 20 ppm.

Accordingly, the present invention also relates to a process as described above wherein the methanol separated off during the work-up has a methyl formate content of less than 500 ppm.

Depending on the requirements made of the purity of the methanol fraction, residues of other components, for example acetaldehyde, 1,1-dimethoxyethane, propionaldehyde, 1,1-dimethoxypropane, acetone or 2,4- dimethyl-1,3-dioxolane, which remain in the methanol fraction after the distillative work-up can be separated from the methanol by one or more suitable measures, for example one or more further distillations.

It is generally entirely sufficient if the concentration of each individual secondary component in the methanol is less than 1% by weight and the sum of all secondary components does not exceed 5% by weight.

The methanol separated from the methyl formate in this way can be re-used, it being in principle conceivable for the methanol to be fed back into the process for the preparation of propylene oxide or, if necessary, fed to a different process in which methanol is required as solvent or as starting material or in another function. It is of course also conceivable to divide the methanol stream resulting from the separation according to the invention into two or more streams, and to feed each stream to a different process.

In a particularly preferred embodiment of the process according to the invention, the methanol which has been separated from the methyl formate and, if present, one or more by-products or impurities is fed back, as described above, into the process for the preparation of propylene oxide. The methanol is preferably, inter alia, pumped into a buffer tank and fed into the process therefrom.

Accordingly, the present invention also relates to a process as described above wherein the methanol separated from the methyl formate in the course of the work-up is fed back into the process.

The preparation of propylene oxide can in principle be carried out by any processes which are carried out in the presence of methanol.

In a preferred embodiment of the process according to the invention, the propylene oxide is prepared from propene and hydrogen peroxide in at least one reaction step in the presence of methanol, giving a mixture comprising methanol, propylene oxide and water.

The reaction of propene with hydrogen peroxide can be carried out here by any suitable methods. For example, the preparation of propylene oxide can be carried out in a batch process or continuously.

With respect to the continuous processes, all suitable reactor arrangements are again conceivable. Thus, for example, the propylene oxide can be prepared in a cascade of two or more reactors connected to one another in series. Conceivable processes are likewise those in which reactors arranged in parallel are employed. Combinations of these processes are also possible. In the case where two or more reactors are connected in series, suitable intermediate treatments can also be provided between the reactors. Reference is made in this connection to, inter alia, PCT/EP99/05740 and DE-A 100 15 246.5, which are expressly incorporated into the present application by way of reference in their full scope with respect to the reactor arrangement and intermediate treatments.

Furthermore, the temperature and pressure of the reaction medium can be modified during the process in the course of the preparation of propylene oxide from propene and hydrogen peroxide. The pH and temperature of the reaction medium can likewise be modified. It is furthermore possible, in addition to the pH and temperature of the reaction medium, additionally to modify the pressure under which the reaction takes place. Reference is made in this respect to DE-A 199 36 547.4, which is expressly incorporated into the present application by way of reference in its full scope in this respect.

The mixture resulting from the preparation of propylene oxide from propene and hydrogen peroxide and comprising methanol, propylene oxide and water is preferably worked up in the process according to the invention by firstly separating off propylene oxide.

In a particularly preferred embodiment, the present invention therefore relates to a process as described above in which (i) in at least one reaction step, propylene oxide is prepared from propene and hydrogen peroxide in the presence of methanol, giving a mixture (Gi) comprising methanol, propylene oxide and water, (ii) the propylene oxide is separated from the mixture (Gi), giving a mixture (Gii) comprising methanol and water, (iii) water is separated from the mixture (Gii), giving a mixture (Giii) comprising methanol and methyl formate, (iv) methanol is separated from the mixture (Giii), and (v) the methanol separated off in (iv) is fed back into (i).

The separation of water in (iii) from the mixture (Gii) is preferably carried out by distillation in the process according to the invention, it being possible to use one or more distillation columns. One or two distillation columns are preferably employed. In the case where heat recovery is unnecessary, one distillation column is preferably employed. Two or more distillation columns are preferably employed if particularly good heat integration in the process is to be ensured.

Regarding the physical parameters, such as temperature or pressure, there are no particular restrictions in the distillative separation of water from the mixture (Gii).

If only one column is employed in the process according to the invention for the separation of water from the mixture (Gii), this column preferably has at least 5, preferably at least 20 and further preferably at least 30 theoretical plates. The distillation is preferably carried out at pressures in the range from 0.5 to 40 bar, preferably from 1.0 to 20 and particularly preferably from 2.0 to 15 bar.

If two columns are employed in the process according to the invention for the separation of water from the mixture (Gii), the pressures are selected so that the heat of condensation at the top of the columns can be used to heat other process streams. This is achieved, for example, by cooling the condenser of at least one column with, for example, water, and using the hot water resulting from the cooling or the steam resulting from the cooling for heating one or more steps of the process according to the invention or alternatively one or more other processes.

The first distillation column is preferably operated at pressures in the range from 0.5 to 40 bar and preferably from 1 to 20 bar. In one possible embodiment, the first column is operated at a higher pressure level than the second column. In this case, the bottom of the second column is heated by means of the condensate from the first column. In a preferred embodiment, the first column is operated at a lower pressure level than the second column. In this case, the bottom of the first column is heated by means of the condensate from the second column.

In a particularly preferred embodiment, the first column is operated at pressures in the range from 4 to 9 bar and further preferably in the range from 6 to 8 bar, and the second column is operated at pressures in the range from 11 to 16 bar and further preferably in the range from 12 to 14 bar. In general, from 20 to 80%, preferably from 30 to 70% and particularly preferably from 40 to 60% of the methanol present in the mixture (Gii) is separated off together with methyl formate at the top of the first column. The mixture obtained at the bottom of the first column is compressed and used as feed for the second column. The top product from the second column comprises the remaining methanol and methyl formate, and the bottom product comprises water. The top product from the first column and the top product from the second column are combined to give the mixture (Giii).

Both in the case of separation of water in two columns and in the case of separation of water in one column, the separation conditions are particularly preferably selected in such a way that the water-content in the mixture (Giii) is generally less than 3% by weight, preferably less than 1% by weight and particularly preferably less than 0.3% by weight. The separation conditions are further preferably selected in such a way that the methanol content in the bottom take-off is less than 5% by weight, preferably less than 1% by weight and particularly preferably less than 0.2% by weight.

The bottom take-off may in addition comprise, as further components, inter alia, for example, methoxypropanols, propylene glycol, formic acid, dipropylene glycol monomethyl ether and formaldehyde.

The present invention therefore also relates to a process as described above wherein the water is separated off in (iii) by distillation, where (w) a mixture (Gw) comprising principally methanol and methyl formate is separated from the mixture (Gii) at the top of a first distillation column, (x) the mixture obtained at the bottom of the first distillation column is used as feed for a second distillation column, (y) a mixture (Gy) comprising principally methanol and methyl formate is obtained at the top of the second distillation column, and (z) the mixtures (Gw) and (Gy) are combined to give the mixture (Giii).

As described above, the propylene oxide prepared in (i) is firstly separated from the mixture (Gi) before water is separated from the resultant mixture (Gii). This separation can likewise generally be carried out by any suitable methods, with distillative separation again being preferred.

If the mixture (Gi) here comprises no or a negligibly small amount of propene which has not been reacted in (i), it is in principle possible to separate propylene oxide from the mixture (Gi) directly in (ii).

In general, however, the mixture (Gi) in the process according to the invention comprises sufficient unreacted propene for its separation to be necessary. In this case, the process is preferably carried out by separating unreacted propene from the mixture (Gi) in a first step, and separating the propylene oxide from the resultant mixture comprising propylene oxide.

Accordingly, the present invention also relates to a process as described above wherein the separation of the propylene oxide in (ii) is carried out in at least two steps (a) and (b), where (a) propene is separated from the mixture (Gi), which, in addition to methanol, propylene oxide and water, comprises propene which has not reacted in (i), giving a mixture (Ga) comprising methanol, propylene oxide and water, and (b) propylene oxide is separated from the mixture (Ga) to give the mixture (Gii).

While all suitable methods are again possible for these separations in (a) and (b), distillative methods are preferred.

In principle, as described above, propene and propylene oxide, for example, can be separated from the mixture (Gi) in a single distillation column, with, for example, the propylene oxide being separated off via the side take-off and the propene at the top, in which case a mixture comprising methanol and water is obtained at the bottom.

Preferably, however, use is made of at least two separate columns, with the propene preferably being taken off at the top of at least one column, and a mixture (Ga) comprising propylene oxide, methanol and water being obtained at the bottom. Propylene oxide is preferably separated from the mixture (Ga) at the top of at least one further column, with the mixture (Gii) being obtained at the bottom.

Preference is given to a column in which the distillative separation in (a) is carried out in a column generally having at least 5, preferably at least 10 and particularly preferably at least 15 theoretical plates, at pressures in the range from, in general, from 0.2 to 25 bar, preferably from 0.5 to 5 bar and particularly preferably approximately 1 bar. The temperature at which propene is separated off at the top is particularly preferably here approximately 25° C. at the particularly preferred pressure of approximately 1 bar. The temperature at which the mixture comprising methanol, water and propylene oxide is separated off at the bottom is particularly preferably here approximately 63° C. at the particularly preferred pressure of approximately 1 bar.

As far as the distillative separation in (b) is concerned, preference is given in the process according to the invention to methods in which a column generally having at least 20, preferably at least 40 and particularly preferably at least 60 theoretical plates is operated at pressures of in general in the range from 0.3 to 10 bar, preferably from 0.5 to 5 bar and particularly preferably from 0.6 to 1.2 bar. The temperature at which propylene oxide is separated off at the top is approximately 26° C. here at a pressure of approximately 0.75 bar. The temperature at which the mixture comprising methanol and water is separated off at the bottom is approximately 67° C. here at a pressure of approximately 0.75 bar.

The present invention therefore also relates to a process as described above wherein the separations in (a) and (b) are carried out by distillation at (a) a pressure in the range from 0.2 to 25 bar in a column having at least 5 theoretical plates, and (b) a pressure in the range from 0.3 to 10 bar in a column having at least 20 theoretical plates.

The propene separated off in (a) is, in a particularly preferred embodiment of the process according to the invention, fed back into (i) as starting material. Under certain circumstances, the problem occurs here that, on separation of the propene as low-boiling fraction, as described above, oxygen can accumulate in the low-boiling fraction in a concentration which converts the low-boiling fraction into an ignitable mixture. This can result in a serious safety risk if propene is separated off from the low-boiling fraction by distillation and fed back into (i). This problem can be solved, for example, by removing propene from the low-boiling fraction by distillation and adding an inert substance having a boiling point which is lower than that of propene, preferably methane, into the upper part of the separation device used for this purpose in such an amount that the oxygen is diluted to a concentration at which the mixture is no longer ignitable. This method is described, for example, in EP-B 0 719 768. However, the problem is preferably solved by using a method for the workup of a mixture comprising propene and oxygen in which oxygen is removed from the mixture by distillation to give a further mixture, and the propene is removed from the further mixture by distillation. This method is described in DE-A 100 01 401.1, which is expressly incorporated into the present invention by way of reference in its full scope in this respect.

In principle, methanol can be employed as solvent in the process described above and, besides methanol, one or more further suitable solvents can be used. This at least one further solvent can likewise be worked up like methanol and fed back into the process. Further solvents of this type are, inter alia, water,
alcohols, preferably lower alcohols, further preferably alcohols having less than 6 carbon atoms, for example ethanol, propanols, butanols and pentanols,
diols or polyols, preferably those having less than 6 carbon atoms,
ethers, for example diethyl ether, tetrahydrofuran, dioxane, 1,2-diethoxyethane and 2-methoxyethanol,
esters, for example methyl acetate or butyrolactone,
amides, for example dimethylformamide, dimethylacetamide and N-methylpyrrolidone,
ketones, for example acetone,
nitriles, for example acetonitrile,
or mixtures of two or more of the above-mentioned compounds.

Suitable catalysts for the conversion of propylene into propylene oxide are in principle all catalysts, preferably all heterogeneous catalysts, which are suitable for the respective reaction. Preference is given here to catalysts which comprise a porous oxidic material, for example a zeolite. Preference is given to catalysts in which the porous oxidic material is a titanium-, vanadium-, chromium-, niobium- or zirconium-containing zeolite.

In particular, zeolites exist which contain no aluminum and in which some of the Si(IV) in the silicate lattice has been replaced by titanium in the form of Ti(IV). The titanium zeolites, in particular those having a crystal structure of the MFI type, and methods for their preparation are described, for example, in EP-A 0 311 983 and EP-A 0 405 978.

Titanium zeolites having an MFI structure are known for the fact that they can be identified via a certain pattern in the determination of their X-ray diffraction diagrams and in addition via a skeletal vibration band in the infrared region (IR) at about 960 cm$^{-1}$ and thus differ from alkali metal titanates or crystalline or amorphous $TiO_2$ phases.

Suitable here are, in detail, titanium-, vanadium-, chromium-, niobium- and zirconium-containing zeolites having a pentasil zeolite structure, in particular the types with X-ray assignment to the ABW, ACO, AEI, AEL, AEN, AET, AFG, AFI, AFN, AFO, AFR, AFS, AFT, AFX, AFY, AHT, ANA, APC, APD, AST, ATN, ATO, ATS, ATT, ATV, AWO, AWW, BEA, BIK, BOG, BPH, BRE, CAN, CAS, CFI, CGF, CGS, CHA, CHI, CLO, CON, CZP, DAC, DDR, DFO, DFT, DOH, DON, EAB, EDI, EMT, EPI, ERI, ESV, EUO, FAU, FER, GIS, GME, GOO, HEU, IFR, ISV, ITE, JBW, KFI, LAU, LEV, LIO, LOS, LOV, LTA, LTL, LTN, MAZ, MEI, MEL, MEP, MER, MFI, MFS, MON, MOR, MSO, MTF, MTN, MTT, MTW, MWW, NAT, NES, NON, OFF, OSI, PAR, PAU, PHI, RHO, RON, RSN, RTE, RTH, RUT, SAO, SAT, SBE, SBS, SBT, SFF, SGT, SOD, STF, STI, STT, TER, THO, TON, TSC, VET, VFI, VNI, VSV, WEI, WEN, YUG or ZON structure and to mixed structures consisting of two or more of the above-mentioned structures. Also feasible for use in the process according to the invention are titanium-containing zeolites having the UTD-1, CIT-1 or CIT-5 structure. Further titanium-containing zeolites which may be mentioned are those having the ZSM-48 or ZSM-12 structure.

Ti zeolites having the MFI, MEL or MFI/MEL mixed structure are regarded as particularly preferred for the process according to the invention. Preference is furthermore given, in detail, to the Ti-containing zeolite catalysts generally known as "TS-1", "TS-2" and "TS-3", and Ti zeolites having a skeletal structure which is isomorphous with β-zeolites.

In the process according to the invention, particular preference is given to a heterogeneous catalyst comprising the titanium-containing silicalite TS-1.

Accordingly, the present invention also relates to a process as described above wherein the propylene oxide is prepared using a zeolite catalyst, preferably a titanium silicalite catalyst and in particular a titanium silicalite catalyst of the TS-1 structure.

It is possible in the process according to the invention for the catalyst used to be the porous oxidic material itself. However, it is of course also possible for the catalyst employed to be a molding comprising the porous oxidic material. The molding here can be produced, starting from the porous oxidic material, by any prior-art processes.

If it should be necessary for the purposes of the process according to the invention, the catalyst employed can be regenerated. Such processes are described, for example, in DE-A 100 15 246.5, which is expressly incorporated herein by way of reference in this respect.

In the following examples, the present invention is explained in greater detail.

EXAMPLES

Comparative Example

A mixture of methanol, 30% strength by weight aqueous hydrogen peroxide solution and propene in the weight ratio 64.5:15.5:20 was reacted in an autoclave containing TS-1 powder at 0° C. under the autogenous pressure until the hydrogen peroxide conversion was greater than 99%.

The reactor contents were subsequently passed into a bubble-cap tray, cooled to 0° C., of a distillation apparatus via a rising pipe with installed filter serving to retain the catalyst.

The crude product was then distilled, and the fraction boiling in the range from 33 to 36° C. and comprising the propylene oxide was collected.

The distillation was then continued, and the cut (S) having a boiling point in the range from 56 to 66° C. was collected. The cut essentially comprised all the methanol with small amounts of acetaldehyde (from about 0.3 to 0.6% by weight), acetone (from about 0.1 to 0.3% by weight), 1,1-dimethoxyethane (from about 0.4 to 0.8% by weight) and methyl formate (from about 50 to 120 ppm). The % by weight data are in each case based on the weight of the cut.

The above-described reaction of propene was subsequently repeated with the methanol cut (S) as solvent. Distillation of the resultant crude product gave a propylene oxide cut (distillation fraction in the range from 33 to 36° C.) which had a methyl formate content in the range from 1000 to 2500 ppm.

Example According to the Invention

The first reaction and the first distillation were repeated as in the comparative example.

The resultant methanol cut (S) was subjected to a second distillation using a column having at least ten theoretical plates. Top product was taken off until the top temperature exceeded 58° C. In total, about 1% of the methanol fraction employed were distilled off as top product. The bottom product which remained contained less than 10 ppm of methyl formate.

With this recovered methanol as bottom product, the reaction of the propene with hydrogen peroxide was repeated.

Distillation of the resultant crude products gave a propylene oxide cut (distillation fraction in the range from 33 to 36° C.) which had a methyl formate content in the range below 10 ppm.

The methyl formate content was in each case determined by gas chromatography.

We claim:

1. A process for the preparation of propylene oxide comprising forming propylene oxide in the presence of methanol, wherein a first mixture comprising propylene oxide and methanol is formed, separating propylene oxide from the first mixture to form a second mixture comprising methanol, and separating methanol from a mixture comprising methanol and methyl formate, wherein methyl formate is formed during the process.

2. The process as claimed in claim 1, wherein the methanol is separated from the mixture comprising methanol and methyl formate in a distillation column having at least 5 theoretical plates at 0.2 to 50 bar.

3. The process as claimed in claim 1, wherein the methanol separated from the mixture comprising methanol and methyl formate has a methyl formate content of less than 500 ppm.

4. The process as claimed in claim 1, further comprising feeding the methanol separated from the mixture comprising methanol and methyl formate back into the process.

5. The process as claimed in claim 1, comprising (i) forming propylene oxide from propene and hydrogen peroxide in the presence of methanol, to form a mixture (Gi) comprising methanol, propylene oxide and water, (ii) separating the propylene oxide from the mixture (Gi), to form a mixture (Gii) comprising methanol and water, (iii) separating water from the mixture (Gii), to form a mixture (Gui) comprising methanol and methyl formate, (iv) separating methanol from the mixture (Giii), and (v) feeding the methanol separated from the mixture (Giii) back into (i).

6. The process as claimed in claim 5, wherein the water is separated by distillation in (iii), wherein (w) a mixture (Gw) comprising principally methanol and methyl formate is separated from the mixture (Gii) at the top of a first distillation column.

(x) the mixture obtained at the bottom of the first distillation column is fed into a second distillation column, (y) a mixture (Gy) comprising principally methanol and methyl formate is obtained at the top of the second distillation column, and (z) the mixtures (Gw) and (Gy) are combined to give the mixture (Giii).

7. The process as claimed in claim 5, wherein the mixture G(i) further comprises propene and in (ii) is separated by at least (a) and (b), where (a) propene is separated from the mixture (Gi), to form a mixture (Ga) comprising methanol, propylene oxide and water, and (b) propylene oxide is separated from the mixture (Ga) to give the mixture (Gii).

8. The process as claimed in claim 7, wherein the separating in (a) and (b) is canied out by distillation at a) a pressure of from 0.2 to 25 bar in a column having at least 5 theoretical plates, and b) a pressure of from 0.3 to 10 bar in a column having at least 20 theoretical plates.

9. The process as claimed in claim 7, wherein the mixture (Ga) further comprises methyl formate.

10. The process as claimed in claim 5, wherein the mixture (Gi) further comprises methyl formate.

11. The process as claimed in claim 5, wherein the mixture (Gii) further comprises methyl formate.

12. The process as claimed in claim 1, wherein the propylene oxide is formed in the presence of a zeolite.

13. The process as claimed in claim 1, wherein the propylene oxide is formed in the presence of a titanium silicalite catalyst.

14. The process as claimed in claim 1, wherein the propylene oxide is formed in the presence of a titanium silicalite catalyst having the TS-1 structure.

15. The process as claimed in claim 1 wherein the methanol is separated from the mixture comprising methanol and methyl formate in a distillation column having at least 10 theoretical plates.

16. The process as claimed in claim 1 wherein the methanol is separated from the mixture comprising methanol and methyl formate in a distillation column having at least 20 theoretical plates.

17. The process as claimed in claim 1, wherein the methanol separated from the mixture comprising methanol and methyl formate has a methyl formate content of less than 100 ppm.

18. The process as claimed in claim 1, wherein the methanol separated from the mixture comprising methanol and methyl formate has a methyl formate content of less than 20 ppm.

19. The process as claimed in claim 1, further comprising separating at least one of acetaldehyde, 1,1-dimethoxyethane, propionaldehyde, 1,1-dimethoxypropane, acetone or 2,4-dimethyl-1,3-dioxolane from a the mixture comprising methanol and methyl formate.

20. The process as claimed in claim 1, wherein separating methanol from a mixture comprising methanol and methyl formate includes distilling.

21. The process as claimed in claim 1, wherein the first mixture further comprises methyl formate.

22. The process as claimed in claim 1, wherein the second mixture further comprises methyl formate.

* * * * *

UNITED STATES PATENT AND TRADEMARK OFFICE
CERTIFICATE OF CORRECTION

PATENT NO. : 6,849,162 B2
DATED : February 1, 2005
INVENTOR(S) : Teles et al.

It is certified that error appears in the above-identified patent and that said Letters Patent is hereby corrected as shown below:

<u>Title page,</u>
Items [45] and [*] Notice, should read
-- Date of Patent: *Feb. 1, 2005
[*] Notice:   Subject to any disclaimer, the term of this patent is extended or adjusted under 35, U.S.C. 154(b) by 0 days.

This Patent is subject to a terminal disclaimer. --

Signed and Sealed this

Tenth Day of May, 2005

JON W. DUDAS
*Director of the United States Patent and Trademark Office*